(12) United States Patent
Reilly

(10) Patent No.: US 8,340,244 B1
(45) Date of Patent: Dec. 25, 2012

(54) VACUUM INTERFACE ASSEMBLY

(75) Inventor: Francis Reilly, Bayport, NY (US)

(73) Assignee: Ceres Technologies, Inc., Saugerties, NY (US)

( * ) Notice: Subject to any disclaimer, the term of this patent is extended or adjusted under 35 U.S.C. 154(b) by 245 days.

(21) Appl. No.: 12/925,361

(22) Filed: Oct. 20, 2010

Related U.S. Application Data

(60) Provisional application No. 61/279,434, filed on Oct. 21, 2009.

(51) Int. Cl.
*G01N 23/223* (2006.01)

(52) U.S. Cl. .......................................... 378/44

(58) Field of Classification Search ...................... 378/44
See application file for complete search history.

*Primary Examiner* — Jurie Yun

(74) *Attorney, Agent, or Firm* — Heslin Rothenberg Farley & Mesiti P.C.

(57) ABSTRACT

An X-ray metrology system for a vacuum deposition chamber includes a vacuum interface assembly mounted through an aperture in the exterior wall of the chamber and extending into the interior of the chamber. The interface assembly is formed from a housing having side walls and a bottom forming an interior chamber, and an X-ray port mounted in an aperture in the bottom of the housing. The X-ray port has two apertures therethrough, with each aperture being covered by a window of beryllium. An X-ray metrology machine having a generator and detector is disposed within the housing, and the apertures in the X-ray port are arranged so that X-rays generated by the generator pass through one of the apertures, and X-rays fluorescing off of a substrate in the deposition chamber travel through the other aperture to the detector.

12 Claims, 8 Drawing Sheets

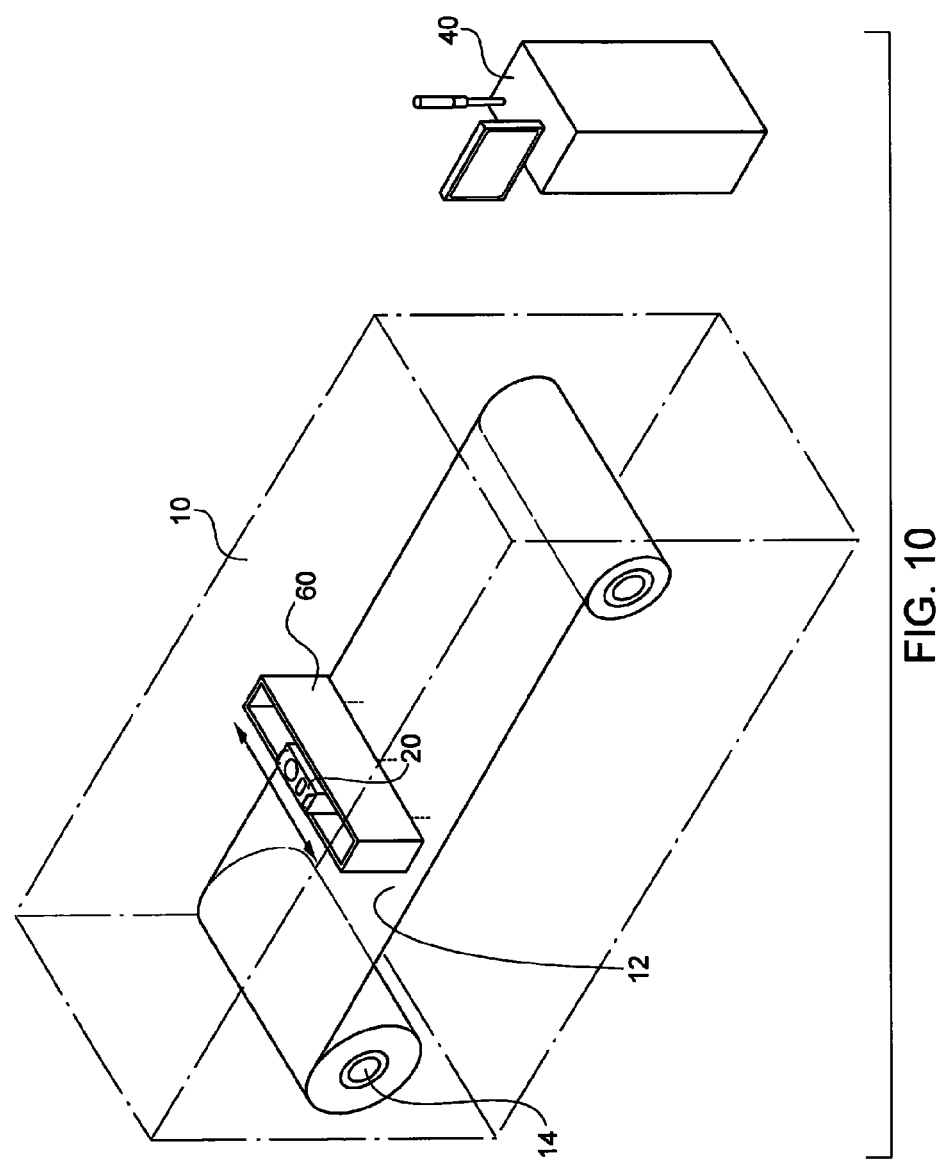

VACUUM INTERFACE ASSEMBLY

CROSS-REFERENCE TO RELATED APPLICATIONS

This application claims priority under 35 USC §119(e) of U.S. Provisional Application Ser. No. 61/279,434, filed on Oct. 21, 2009.

BACKGROUND OF THE INVENTION

1. Field of the Invention

This invention relates to an assembly for protecting an X-ray head from the heat generated in a vacuum XRF film metrology system. In particular the invention relates to a containment vessel that protects the X-ray head while allowing X-rays to penetrate through a port in the vessel to reach the substrate, and enter back through the port to a detector in the head assembly.

2. The Prior Art

X-ray based metrology tools are required to manufacture the active layer in copper indium gallium diselenide photovoltaic cells (CIGS PV cells) that convert sunlight to electricity. Vacuum-based processes that deposit CIGS films must be controlled in a vacuum environment to ensure acceptable commercial output. Venting to air for process control would destroy the solar material. As a result, X-ray fluorescence (XRF) analysis of the integrity of the film stack (thickness and composition determination) must be performed in a vacuum. This allows adjustment of the deposition process tool to maintain engineered film tolerances. Vacuum-based CIGS PV manufacture requires real-time information that allows correction of process deviation immediately without losing vacuum to eliminate final PV film conversion efficiency output losses. XRF measurement data is required to manage yield and optimize conversion efficiencies for maximum resultant electric output of the PV material.

X-ray based metrology tools are expensive and delicate instruments that will not survive in a high temperature (500° C.) vacuum environment typical of internal CIGS and related film deposition chambers. The XRF tool must reside outside the deposition chamber to ensure tool survival and measurement capability. Typical stainless steel wall thicknesses for process deposition tools are about 0.5 to 1.0 inch, which will not allow X-ray frequency range radiation at the fluorescent power levels used in film metrology to penetrate these wall thicknesses.

SUMMARY OF THE INVENTION

It is therefore an object of the invention to provide a device that allows penetration of X-rays into the deposition chamber while protecting the X-ray metrology tool.

This object is accomplished by a system that comprises an X-ray head module and a vacuum interface that supports the head module. The x-ray head module includes the x-ray generation and detection columns and the head control electronics, communications and cooling systems. The remote x-ray head provides flexibility to mate with a variety of vacuum equipment configurations. The head is mounted in a stainless steel containment vessel forming the interface that provides radiation shielding and incorporates one or more ports that allow x-rays to pass through the process deposition tool wall into the vacuum process tool environment or section of the vacuum process line environment. The vacuum interface is custom-fabricated to accommodate the specific mechanical requirements of a specific process tool or line. Preferably, the bottom of the vessel lies approximately 0.5" (10 mm) from the substrate surface, and the incident x-ray beam is perpendicular to the measurement point. This height and orientation provides optimal measurement precision while ensuring that no contact occurs with the coated substrate material. X-ray ports are integrated into the base of the containment vessel. The ports allow primary beam x-rays to pass into the clean vacuum section of the deposition tool and enables X-rays fluoresced by the sample to be captured by the detector. The X-ray port is a stainless steel puck that has two apertures in it. The first aperture allows primary beam X-rays to enter the process vessel, and the second aperture allows fluoresced X-rays from the photovoltaic product to leave the process vessel. Fluoresced X-rays are counted by the X-Ray head's detector system. Beryllium windows cover the apertures in the X-ray interface port assembly. A 5 mm thickness at a 0.5 inch lateral span for each window provides sufficient axial load capacity to prevent failure at $10^{-9}$ torr. In addition, the use of Beryllium reflects infrared radiation that would otherwise strike the detector and cause erroneous measurements. The X-ray port has an o-ring seal that maintains vacuum between itself and the interface housing. The vacuum interface housing has an o-ring seal that maintains vacuum between itself and the wall of the vacuum chamber. This system (X-ray head, vacuum interface housing and X-ray vacuum interface port(s), enables XRF measurements to be performed with the X-ray head remaining in an air environment.

BRIEF DESCRIPTION OF THE DRAWINGS

Other objects and features of the present invention will become apparent from the following detailed description considered in connection with the accompanying drawings. It is to be understood, however, that the drawings are designed as an illustration only and not as a definition of the limits of the invention.

In the drawings, wherein similar reference characters denote similar elements throughout the several views:

FIG. 10 is a perspective view of the system showing a linear X-ray head.

DETAILED DESCRIPTION OF THE EMBODIMENTS

Figure 1:
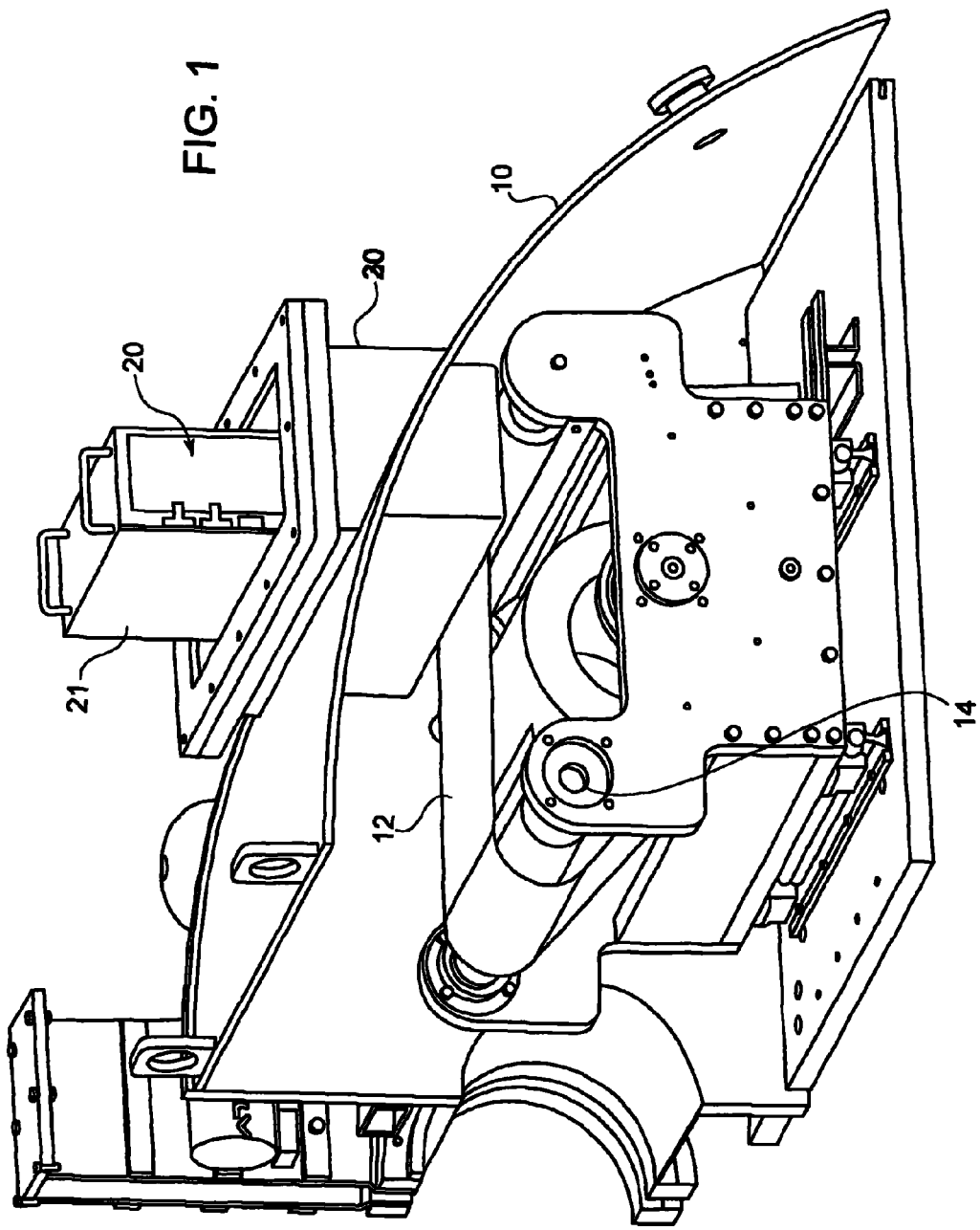
FIG. 1 shows a side view in partial cross-section of the vacuum deposition chamber, interface vessel and X-ray head according to one embodiment of the invention.
Figure 2:
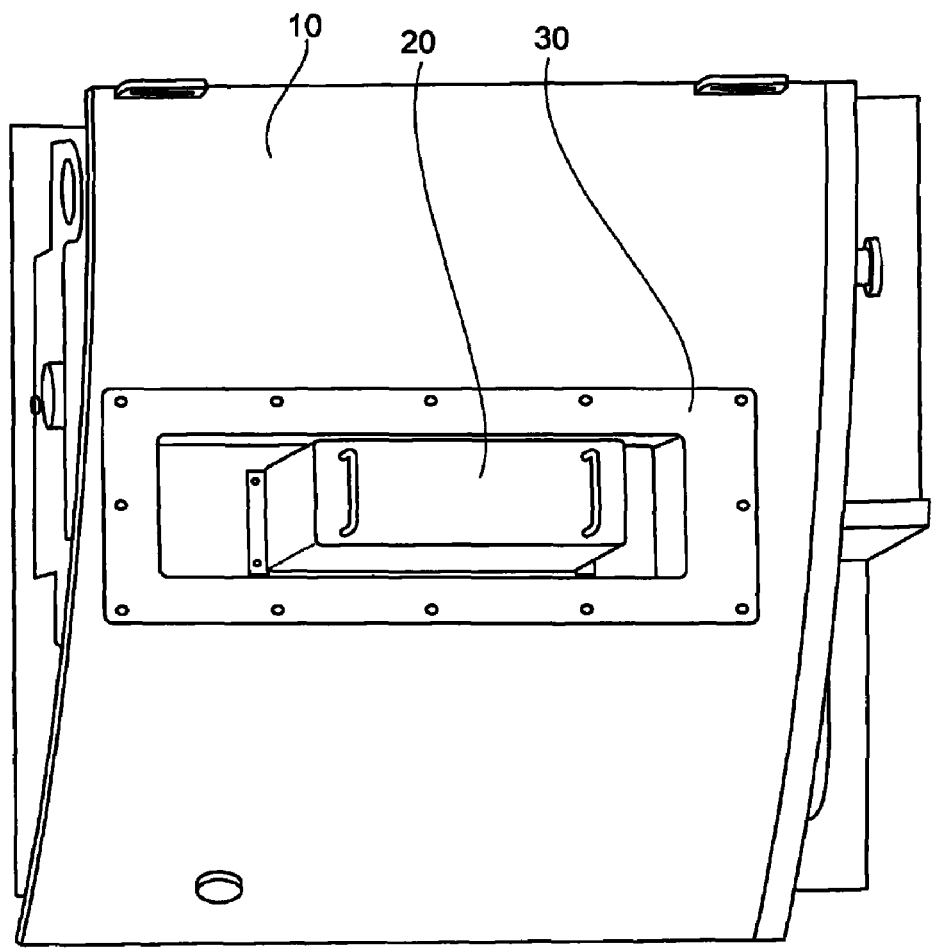
FIG. 2 shows a top view of the system according to FIG. 1.

Referring now in detail to the drawings, FIGS. 1 and 2 show a vacuum deposition chamber 10 in which a substrate is unwound from a roll 14 for inspection by an X-ray metrology machine 20. Metrology machine 20 is mounted in a vacuum interface assembly 30, which is mounted through a hole in vacuum deposition chamber 10, and sealed to maintain the vacuum within chamber 10. This sealing can be done via an O-ring or by any known method.

Figure 3:
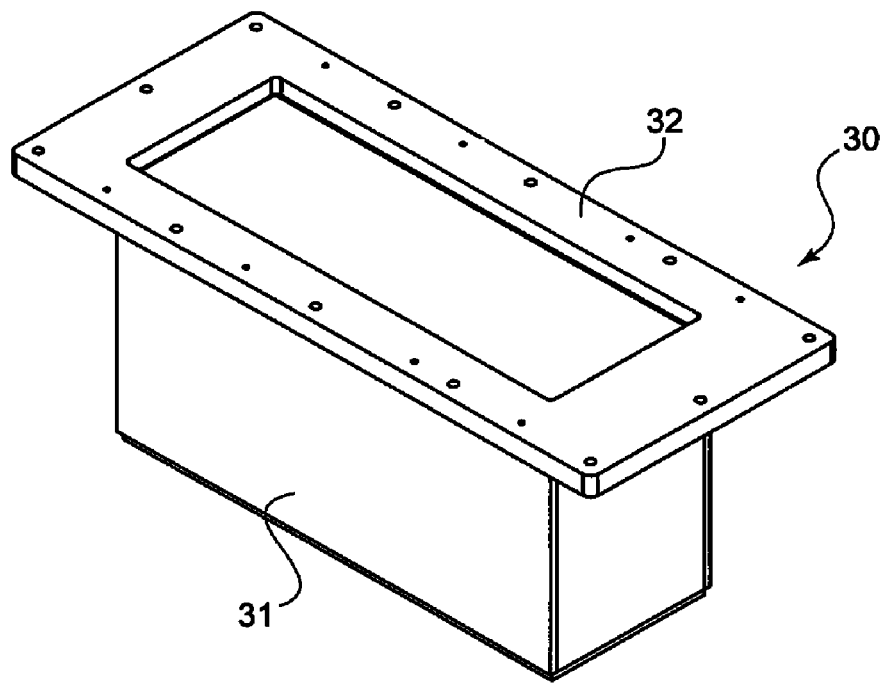
FIG. 3 shows a perspective view of the vacuum interface assembly according to the invention.
Figure 4:
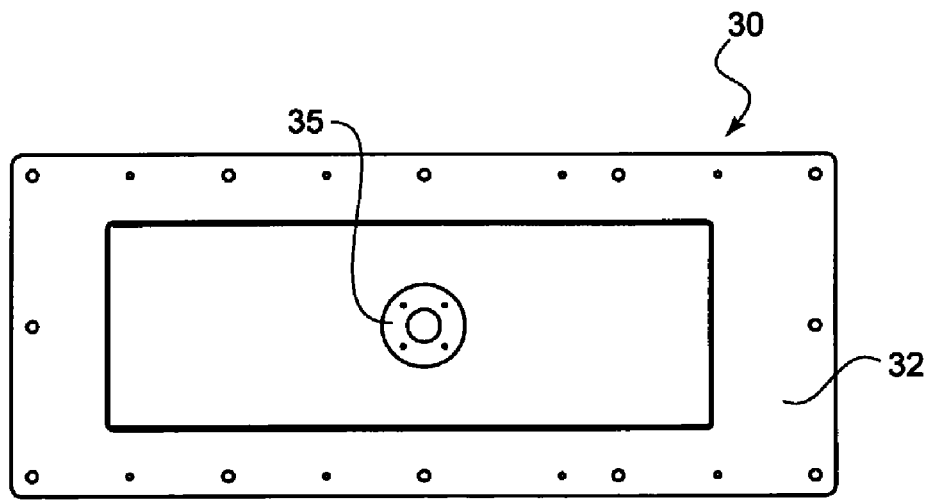
FIG. 4 is a top view of the vacuum interface assembly according to FIG. 3.

As shown in FIGS. 3 and 4, vacuum interface assembly 30 comprises a housing 31 surrounded by an upper flange 32. The housing can be configured to fit metrology machines of different sizes and can be used for a static mounted machine or a linear machine, as described below with regard to FIGS. 9 and 10. At the bottom of housing 31 is an X-ray port 35.

Figure 5:
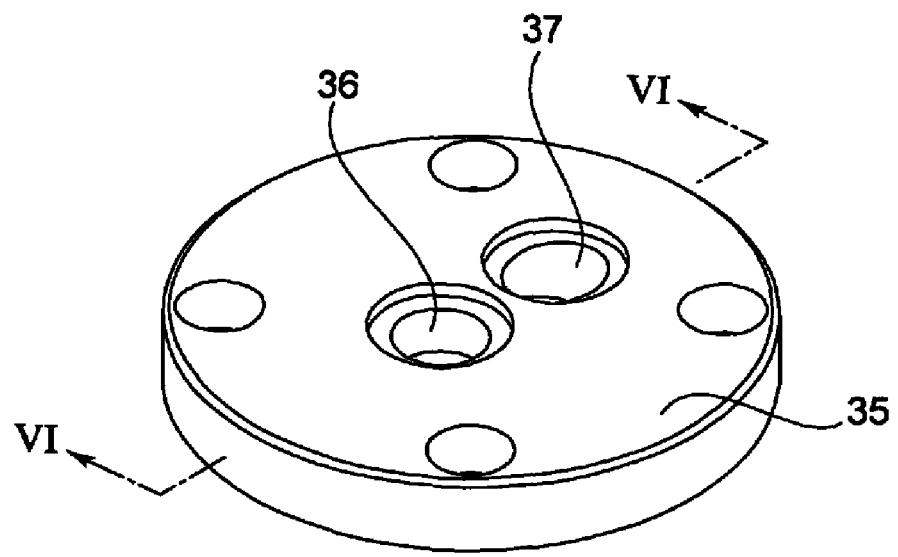
FIG. 5 is a perspective view of the X-ray port according to the invention.
Figure 6:
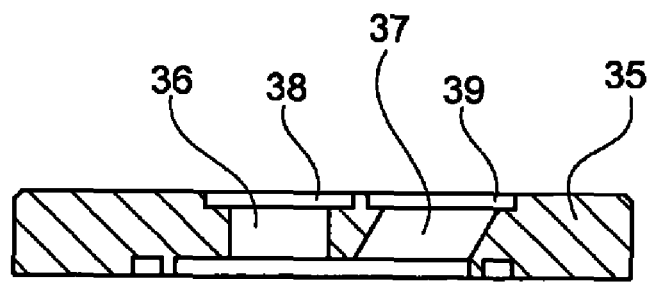
FIG. 6 is a cross-sectional view along lines VI-VI of FIG. 5.

X-ray port 35 is a steel cylinder through which two apertures 36, 37 extend, as shown in FIGS. 5 and 6. As shown in FIG. 6, aperture 36 extends through port 35 perpendicular to the plane of port 35. Aperture 37 extends at an angle other than 90 degrees to the plane of the port. Covering each of apertures 36, 37 is a beryllium window 38, 39, respectively. Beryllium windows 38, 39 allow X-rays to pass through to and from substrate 12 while protecting X-ray metrology machine 20 and maintaining the vacuum inside chamber 10.

Figure 7:
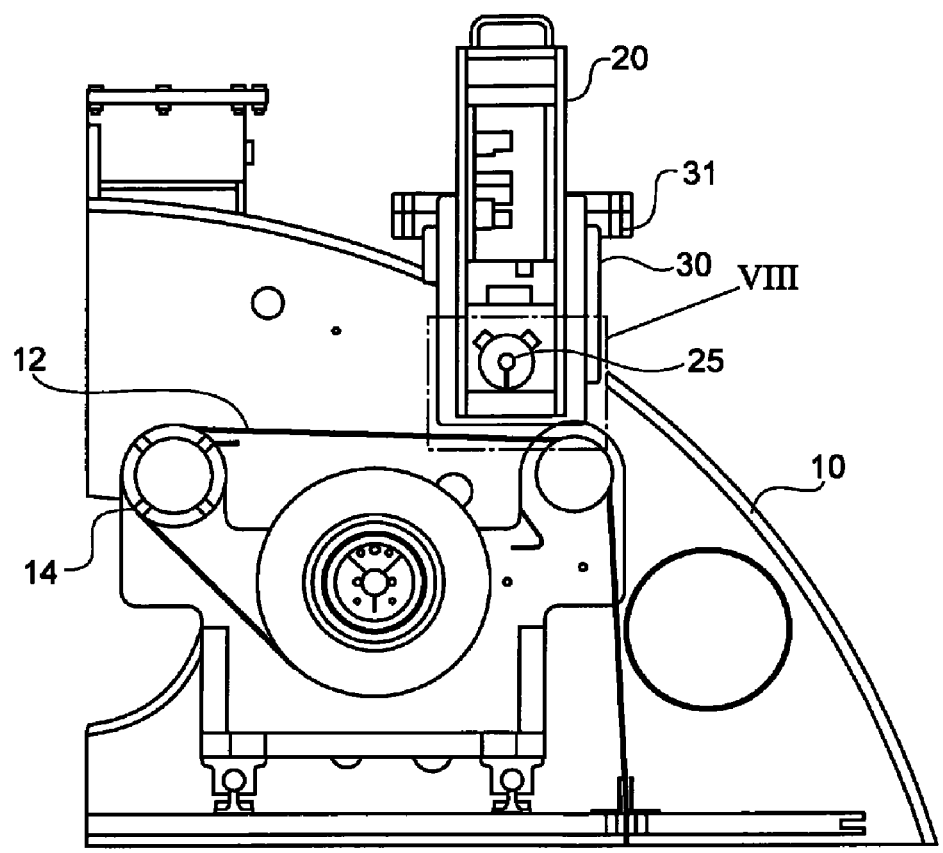
FIG. 7 is a cross-sectional view of the system shown in FIG. 1.

As shown in FIG. 7, X-ray metrology machine 20 with X-ray generator 25 is mounted within vacuum interface assembly 30, and extends into the cavity of vacuum chamber 10. Vacuum interface assembly 30 is positioned so that X-rays from generator 25 can reach substrate 12 as it is unrolled from roll 14. In general, the bottom of machine 20 is preferably positioned approximately 0.5 inches above the substrate 12, to allow for accurate measurements.

Figure 8:
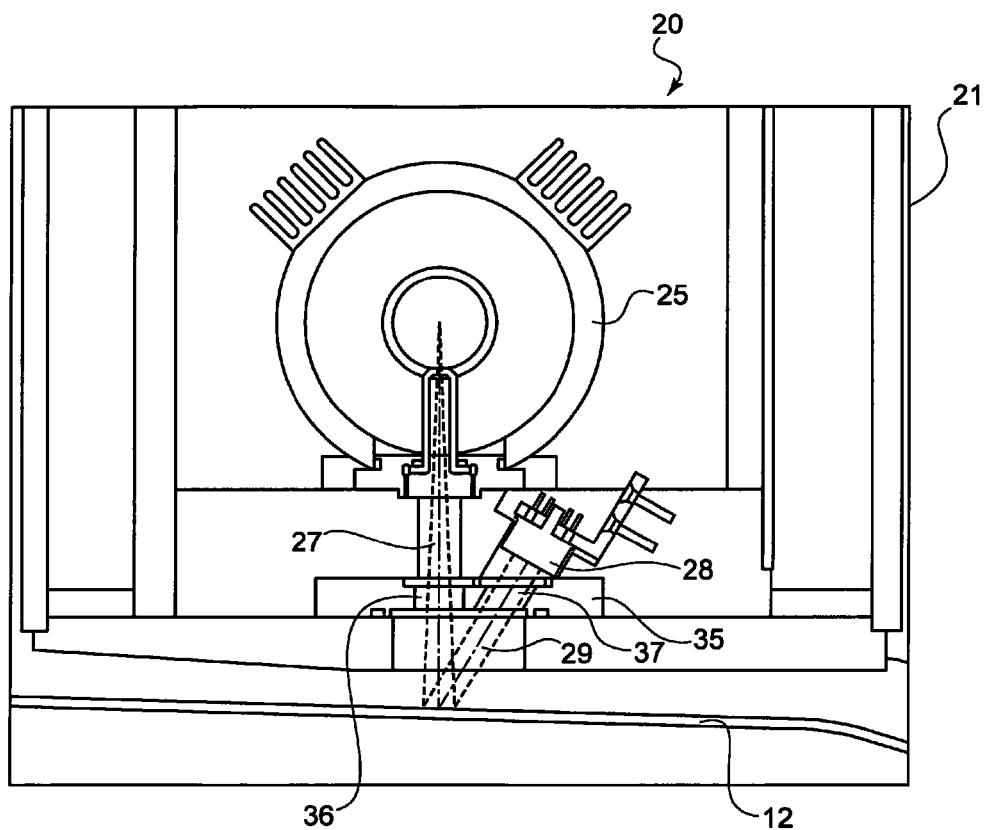
FIG. 8 is an enlarged view of box VIII from FIG. 7.

FIG. 8 shows a detail of the X-ray metrology machine 20 in operation. As substrate 12 passes under machine 20, X-rays 27 generated from generator 25 pass through aperture 36 to substrate 12. The X-rays 29 fluorescing off of substrate 12 then pass upward through aperture 37 to reach detector 28. Information from detector 28 is then sent to a control station 40 (see FIGS. 9 and 10) for analysis of the substrate. The beryllium windows covering apertures 36 and 37 ensure that infrared radiation from the substrate does not affect the measurements of X-ray metrology machine 10, and yet allows X-rays to penetrate to reach substrate 12.

Figure 9:
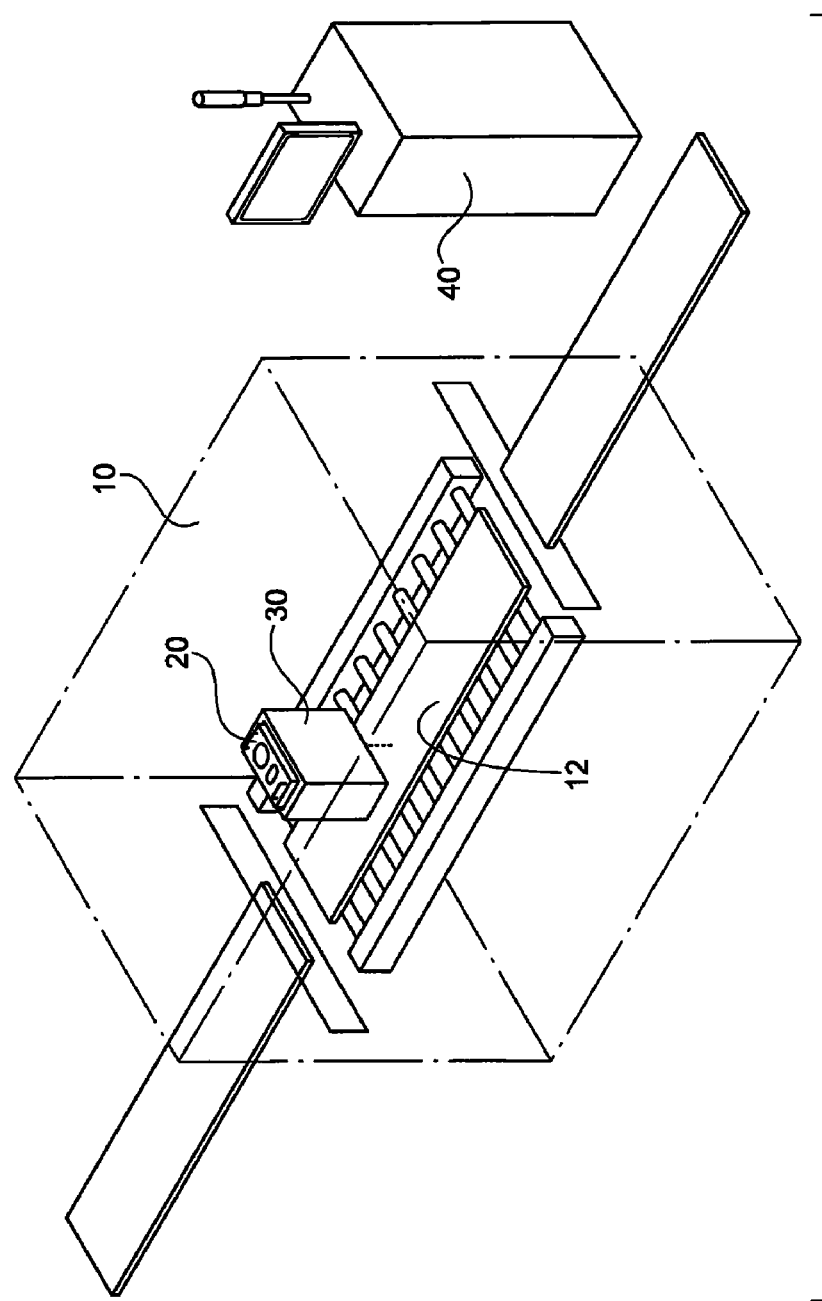
FIG. 9 is a perspective view of the system showing a static X-ray head.

FIGS. 9 and 10 show two different ways the vacuum interface assembly can function. In FIG. 9, vacuum interface assembly 30 is structured to fit closely around metrology machine 20, which remains fixed during analysis of substrate 12. However, as shown in FIG. 10, for larger substrates, a linearly movable arrangement is preferable, so that the entire width of the substrate can be tested. In FIG. 10, vacuum interface assembly 60 is wider than X-ray metrology machine 20. Machine 20 is mounted in vacuum interface assembly 60 so that it can move along the width of interface 60 and take measurements in several different locations along the width of substrate 12. Several of X-ray ports 35 can be mounted in the bottom of vacuum interface assembly 60 to allow for the several different measurements.

Accordingly, while only a few embodiments of the present invention have been shown and described, it is obvious that many changes and modifications may be made thereunto without departing from the spirit and scope of the invention.

What is claimed is:

1. A vacuum interface assembly comprising:
   a housing having side walls and a bottom forming an interior chamber adapted to receive an X-ray metrology machine; and
   an X-ray port mounted in an aperture in the bottom, the X-ray port having two apertures therethrough, with each aperture being covered by a window comprising beryllium.

2. The vacuum interface assembly according to claim 1, wherein the X-ray port is sealed against the housing with an O-ring.

3. The vacuum interface assembly according to claim 1, wherein a first one of said two apertures is positioned perpendicular to a plane of the X-ray port, and a second one of said two apertures is positioned at an angle other than 90 degrees to the plane of the X-ray port.

4. The vacuum interface assembly according to claim 1, further comprising an outwardly extending flange extending around a perimeter of the housing at a top edge of each of the side walls.

5. An X-ray metrology system comprising:
   a vacuum deposition chamber having an exterior wall and an interior cavity;
   a vacuum interface assembly being mounted through an aperture in the exterior wall and extending into the interior cavity, and being sealed from the interior cavity, said vacuum interface assembly comprising:
     a housing having side walls and a bottom forming an interior chamber; and
     an X-ray port mounted in an aperture in the bottom of the housing, the X-ray port having two apertures therethrough, with each aperture being covered by a window comprising beryllium; and
   an X-ray metrology machine disposed within the housing, said X-ray metrology machine having an X-ray generator and a detector;
   wherein the two apertures in the housing are arranged so that X-rays generated by the generator pass through a first one of said two apertures, and X-rays fluorescing off of a substrate in the deposition chamber travel through a second one of said two apertures to said detector.

6. The system according to claim 5, wherein the housing is sealed against the deposition chamber via an O-ring.

7. The system according to claim 5, wherein the first aperture is arranged perpendicular to a plane of the X-ray port, and the generator is positioned so that the X-rays travel perpendicular to the plane of the X-ray port, through the first aperture.

8. The system according to claim 7, wherein the second aperture is positioned at an angle other than 90 degrees to the plane of the X-ray port, and the detector is positioned offset from the generator to receive X-rays traveling through the second aperture.

9. The system according to claim 5, wherein the X-ray metrology machine is mounted to be stationary within the vacuum interface assembly.

10. The system according to claim 5, wherein the X-ray metrology machine is movable along a length of the vacuum interface housing.

11. The system according to claim 5, wherein the vacuum deposition chamber has a substrate conveyor, and wherein the vacuum interface assembly is mounted so that the windows are positioned approximately 10 mm above a substrate positioned on the conveyor.

12. The system according to claim 5, wherein the windows are approximately 5 mm thick and 0.5 inches in diameter.

* * * * *